United States Patent
Edvardsen et al.

(10) Patent No.: US 9,428,582 B2
(45) Date of Patent: Aug. 30, 2016

(54) METHOD OF TREATING RASH IN PATIENTS UNDERGOING ANTI-EGFR THERAPY

(75) Inventors: Klaus Edvardsen, Klampenborg (DK); Steen Lisby, Frederiksberg (DK); Ole Baadsgaard, Hellerup (DK)

(73) Assignee: GENMAB A/S, Copenhagen (DK)

( * ) Notice: Subject to any disclaimer, the term of this patent is extended or adjusted under 35 U.S.C. 154(b) by 797 days.

(21) Appl. No.: 12/306,436

(22) PCT Filed: Jul. 3, 2007

(86) PCT No.: PCT/DK2007/000334
§ 371 (c)(1),
(2), (4) Date: Oct. 2, 2009

(87) PCT Pub. No.: WO2008/003317
PCT Pub. Date: Jan. 10, 2008

(65) Prior Publication Data
US 2010/0150936 A1 Jun. 17, 2010

(30) Foreign Application Priority Data

Jul. 3, 2006 (DK) .............................. 2006 00915
May 15, 2007 (DK) .............................. 2007 00727
Jun. 22, 2007 (DK) .............................. 2007 00901

(51) Int. Cl.
| | | |
|---|---|---|
| A61K 31/495 | (2006.01) | |
| A61K 39/395 | (2006.01) | |
| C07K 16/28 | (2006.01) | |
| A61K 45/06 | (2006.01) | |
| C07K 16/24 | (2006.01) | |
| A61K 39/00 | (2006.01) | |

(52) U.S. Cl.
CPC ....... *C07K 16/2863* (2013.01); *A61K 39/3955* (2013.01); *A61K 45/06* (2013.01); *C07K 16/244* (2013.01); *A61K 2039/507* (2013.01)

(58) Field of Classification Search
None
See application file for complete search history.

(56) References Cited

U.S. PATENT DOCUMENTS

| | | |
|---|---|---|
| 4,294,852 A | 10/1981 | Wildnauer et al. |
| 4,374,775 A | 2/1983 | Dotz et al. |
| 4,719,239 A | 1/1988 | Muller et al. |
| 4,840,970 A | 6/1989 | Ohasi et al. |
| 4,906,411 A | 3/1990 | Shinnaka et al. |
| 4,966,779 A | 10/1990 | Kirk |
| 5,134,127 A | 7/1992 | Stella et al. |
| 5,155,031 A | 10/1992 | Posner et al. |
| 5,180,747 A | 1/1993 | Matsuda et al. |
| 5,356,636 A | 10/1994 | Schneider et al. |
| 5,376,645 A | 12/1994 | Stella et al. |
| 5,412,125 A | 5/1995 | Philippe et al. |
| 5,510,391 A | 4/1996 | Elson |
| 5,637,741 A | 6/1997 | Matsumoto et al. |
| 5,643,583 A | 7/1997 | Voultoury et al. |
| 5,650,156 A | 7/1997 | Grinstaff et al. |
| 5,770,774 A | 6/1998 | Joo et al. |
| 5,785,976 A | 7/1998 | Westesen et al. |
| 5,885,486 A | 3/1999 | Westesen et al. |
| 5,916,749 A | 6/1999 | Bandman et al. |
| 6,013,665 A | 1/2000 | DeMichele et al. |
| 6,110,891 A | 8/2000 | Pusztai et al. |
| 6,160,007 A | 12/2000 | DeMichele et al. |
| 6,187,822 B1 | 2/2001 | Leibovich |
| 6,207,176 B1 | 3/2001 | Howard et al. |
| 6,264,986 B1 | 7/2001 | Hahnlein et al. |
| 6,383,471 B1 | 5/2002 | Chen et al. |
| 6,426,078 B1 | 7/2002 | Bauer et al. |
| 6,428,949 B1 | 8/2002 | Bandman et al. |
| 6,524,594 B1 | 2/2003 | Santora et al. |
| 6,537,579 B1 | 3/2003 | Desai et al. |
| 6,576,660 B1 | 6/2003 | Liao et al. |
| 6,579,994 B2 | 6/2003 | Sankarasubbier et al. |
| 6,582,710 B2 | 6/2003 | Deckers et al. |
| 6,596,287 B2 | 7/2003 | Deckers et al. |
| 6,599,513 B2 | 7/2003 | Deckers et al. |
| 6,660,306 B2 | 12/2003 | Peshoff |
| 6,696,484 B2 | 2/2004 | Liao et al. |

(Continued)

FOREIGN PATENT DOCUMENTS

| | | |
|---|---|---|
| DE | 3514724 A1 | 10/1986 |
| EP | 0392845 A2 | 10/1990 |

(Continued)

OTHER PUBLICATIONS

Bleeker et al., Dual mode action of human anti-epidermal growth factor receptor monoclonal antibody for cancer therapy, J. Immunol. 173:4699-4707, 2004.*
Skov et al., IL-8 as antibody therapeutic target in inflammatory diseases: reduction of clinical activity in palmoplantar pustulosis, J. Immunol. 181:669-679, 2008.*
Rudikoff et al., Proc. Natl. Acad. Sci. USA, 79L1979, 1982.*
Lamminmaki et al., Chrystal structure of a recombinant anti-estradiol Fab fragment in complex with the 17beta-estradiol, J. Blol. Chem. 276:36687-94, 2001.*
MacCallum et al.,Antibody-antigen interactions: contact analysis and binding site topography, J. Mol. Biol. 262:732-745, 1996.*
Ditzel et al., Determinants of polyreaciveity in a large panel of recombinant human antibodies from HIV-1 infection, J. Immunol. 157:739-349, 1996.*
Barbas et al., Human autoantibody recognition of DNA, PNAS USA, 92:2529-2533, Mar. 1995.*
Barbas et al., Recognition of DNA by synthetic antibodies, J. Am. Chem. Soc. 116:2161-2162, 1994.*

(Continued)

Primary Examiner — Claire Kaufman
(74) Attorney, Agent, or Firm — Nelson Mullins Riley & Scarborough LLP; Jane E. Remillard, Esq.; Christopher L. Frank

(57) ABSTRACT

The invention relates to a method for the treatment of a disease susceptible to anti-EGFR treatment, comprising the step of administering, to a human being in nee thereof, a combination of an anti-EGFR agent and an anti-neutrophil-chemoattracta agent, wherein said anti-neutrophil-chemoattractant agent is administered in a dosage regimen that is sufficient to reduce one or more undesired dermatological side-effects the anti-EGFR agent. In one embodiment, the anti-EGFR agent is an anti-EGF antibody and the anti-neutrophil-chemoattractant agent is an anti-IL-8 antibody.

34 Claims, 1 Drawing Sheet

(56) References Cited

U.S. PATENT DOCUMENTS

| | | |
|---|---|---|
| 6,774,100 B2 | 8/2004 | Vishnupad |
| 6,780,439 B2 | 8/2004 | Wilk |
| 6,979,454 B1 | 12/2005 | Lindahl et al. |
| 7,094,431 B2 | 8/2006 | Peshoff |
| 7,326,690 B2 | 2/2008 | Henry et al. |
| 7,402,557 B2 | 7/2008 | Miller et al. |
| 7,405,188 B2 | 7/2008 | Chen |
| 7,745,494 B2 | 6/2010 | Perez-Soler et al. |
| 2002/0061304 A1 | 5/2002 | Miller et al. |
| 2003/0139353 A1 | 7/2003 | Jackson et al. |
| 2003/0170187 A1 | 9/2003 | Marchal |
| 2004/0040011 A1 | 2/2004 | Bosworth et al. |
| 2004/0047852 A1 | 3/2004 | Kennedy |
| 2004/0062817 A1 | 4/2004 | Peshoff |
| 2004/0081674 A1 | 4/2004 | Franke |
| 2004/0138218 A1 | 7/2004 | Pallen et al. |
| 2004/0265396 A1 | 12/2004 | Peshoff |
| 2005/0048008 A1 | 3/2005 | Gupta |
| 2005/0092969 A1 | 5/2005 | Ueda et al. |
| 2005/0118187 A1 | 6/2005 | Yu |
| 2005/0148521 A1 | 7/2005 | Ben-Sasson et al. |
| 2006/0002439 A1 | 1/2006 | Lee |
| 2006/0058398 A1 | 3/2006 | Kamei et al. |
| 2006/0216342 A1 | 9/2006 | Torchilin et al. |
| 2006/0275504 A1 | 12/2006 | Chen |
| 2007/0025950 A1 | 2/2007 | Elson |
| 2007/0142462 A1 | 6/2007 | Kennedy |
| 2007/0238697 A1 | 10/2007 | Jackson et al. |

FOREIGN PATENT DOCUMENTS

| | | |
|---|---|---|
| EP | 1214930 B1 | 6/2002 |
| JP | 2005-206521 | 8/2005 |
| WO | 94/23023 A1 | 10/1994 |
| WO | 97/39746 A1 | 10/1997 |
| WO | 01/64214 A2 | 9/2001 |
| WO | 01/91740 A1 | 12/2001 |
| WO | 02/13780 A1 | 2/2002 |
| WO | 02/20525 A2 | 3/2002 |
| WO | 02/47642 A1 | 6/2002 |
| WO | 03/018033 A1 | 3/2003 |
| WO | 03/061566 A2 | 7/2003 |
| WO | 03/101415 A1 | 12/2003 |
| WO | 2004/019923 A1 | 3/2004 |
| WO | WO-2004/056847 A2 | 7/2004 |
| WO | WO-2004/058797 A2 | 7/2004 |
| WO | 2005/032523 A1 | 4/2005 |
| WO | 2006/029893 A2 | 3/2006 |
| WO | 2006/056889 A2 | 6/2006 |
| WO | 2006/107827 A1 | 10/2006 |
| WO | 2007/147128 A2 | 12/2007 |
| WO | 2008/004231 A1 | 1/2008 |

OTHER PUBLICATIONS

Asakuma, Junichi et al., "Modulation of Tumor Growth and Tumor Induced Angiogenesis after Epidermal Growth Factor Receptor Inhibition by ZD1839 in Renal Cell Carcinoma," *The Journal of Urology*, vol. 171(1 pt. 1):897-902 (2004).

Bruns, Christiane J. et al., "Epidermal Growth Factor Receptor Blockade with C225 Plus Gemcitabine Results in Regression in Human Pancreatic Carcinoma Growing Orthotopically in Nude Mice by Antiangiogenic Mechanisms," *Clinical Cancer Research*, vol. 6:1936-1948 (2000).

Hochster, Howard S. et al., "Consensus Report of the International Society of Gastrointestinal Oncology on Therapeutic Progress in Advanced Pancreatic Cancer," *Cancer*, vol. 107(4):676-685 (2006).

Karashima, Takashi et al., "Inhibition of Angiogenesis by the Antiepidermal Growth Factor Receptor Antibody ImClone C225 in Androgen-independent Prostate Cancer Growing Orthotopically in Nude Mice," *Clinical Cancer Research*, vol. 8:1253-1264 (2002).

Mascia, Francesca et al., "Blockade of the EGF Receptor Induces a Deranged Chemokine Expression in Keratinocytes Leading to Enhanced Skin Inflammation," *American Journal of Pathology*, vol. 163(1):303-312 (2003).

Perez-Soler, Roman et al., "HER1/EGFR Inhibitor-Associated Rash: Future Directions for Management and Investigation Outcomes from the HER1/EGFR Inhibitor Rash Management Forum," *The Oncologist*, vol. 10(5):345-356 (2005).

Salcedo, Rosalba et al., "Combined Administration of Antibodies to Human Interleukin 8 and Epidermal Growth Factor Receptor Results in Increased Antimetastatic Effects on Human Breast Carcinoma Xenografts," *Clinical Cancer Research*, vol. 8:2655-2665 (2002).

International Search Report for Application No. PCT/DK2007/000334, dated Oct. 9, 2007.

Abdelmohsen, Kotb et al., "Epidermal Growth Factor Receptor Is a Common Mediator of Quinone-induced Signaling Leading to Phosphorylation of Connexin-43," The Journal of Biological Chemistry, vol. 278(40):38360-38367 (2003).

Bae, Eun Young et al., "A New VHR Dual-Specificity Protein Tyrosine Phosphatase Inhibitor from Dendrobium moniliforme," Planta Med., vol. 70:869-870 (2004).

Baselga, J. et al., "Phase I Safety, Pharmacokinetic, and Pharmacodynamic Trial of ZD1839, a Selective Oral Epidermal Growth Factor Receptor Tyrosine Kinase Inhibitor, in Patients With Five Selected Solid Tumor Types," Journal of Clinical Oncology, vol. 20(21):4292-4302 (2002).

Bernier, J. et al., "Consensus guidelines for the management of radiation dermatitis and coexisting acne-like rash in patients receiving radiotherapy plus EGFR inhibitors for the treatment of squamous cell carcinoma of the head and neck," Annals of Oncology, vol. 19(1):142-149 (2007).

Busam, K.J. et al., "Cutaneous side-effects in cancer patients treated with the antiepidermal growth factor receptor antibody C225," British Journal of Dermatology, vol. 144:1169-1176 (2001).

Clark, G.M. et al., "Rash severity is predictive of increased survival with erlotinib HCl," Proceedings of the American Society of Clinical Oncology, vol. 22, Abstr. No. 786 (2003).

Cohen, Ezra E.W. et al., "Phase II Trial of ZD1839 in Recurrent or Metastatic Squamous Cell Carcinoma of the Head and Neck," Journal of Clinical Oncology, vol. 21(10):1980-1987 (2003).

Debeer, Edwin J. et al., "Routes of Administration of Materials Capable of Acting as Vitamin K," Proc. Soc. Exp. Biol and Med., vol. 46:535-537 (1941).

Elson, Melvin L., "Topical Phytonadione (Vitamin K1) in the Treatment of Actinic and Traumatic Purpura," Cosmetic Dermatology, vol. 8(12):25-27 (1995).

Gerling, Norbert et al., "The tyrosine phosphatase inhibitor orthovanadate mimics NGF-induced neuroprotective signaling in rat hippocampal gnaling ippocampal neurons," Neurochemistry International, vol. 44:505-520 (2004).

Lage, Augustin et al., "Targeting epidermal growth factor receptor signaling: early results and future trends in oncology," Annals of Medicine, vol. 35(5):327-336 (2003).

Lee, Kyeong et al., "CD45 Protein-Tyrosine Phosphatase Inhibitor Development," Current Topics in Medicinal Chemistry, vol. 3:797-807 (2003).

Liem, David A. et al., "The Tyrosine Phosphatase Inhibitor Bis(Maltolato)-Oxovanadium Attenuates Myocardial Reperfusion Injury by Opening ATP-Sensitive Potassium Channels," The Journal of Pharmacology and Experimental Therapeutics, vol. 309(3):1256-1262 (2004).

Lorusso, Patricia M., "Phase I Studies of ZD1839 in Patients With Common Solid Tumors," Seminars in Oncology, vol. 30(1, Suppl. 1):21-29 (2003).

Lou, Wendy W. et al., "Effects of Topical Vitamin K and Retinol on Laser-Induced Purpura on Nonlesional Skin," Dermatol. Surg., vol. 25:942-944 (1999).

Matschiner, John T. et al., "Metabolism and Vitamin K Activity of cis Phylloquinone in Rats," J. Nutrition, vol. 102:625-630 (1972).

Page, R.C. et al., "Dermatitis from Topical Application of 2-Methyl-1:4-Naphthoqunone (Synthetic Vitamin K Analogue)," The American Journal of the Medical Sciences, vol. 203:566-569 (1942).

Perea, Sofia et al., "Predictors of Sensitivity and Resistance to Epidermal Growth Factor Receptor Inhibitors," Clinical Lung Cancer, vol. 6(Suppl. 1):S30-S34 (2004).

(56) References Cited

OTHER PUBLICATIONS

Rodeck, Ulrich et al., "EGF-R dependent regulation of keratinocyte survival," Journal of Cell Science, vol. 110:113-121 (1997).

Russell, H.K. et al., "Effect of Topical Application of 2-Methyl-1,4-Naph-Thoquinone (Synthetic Vitamin K Analogue) on the Prothrombin Level of Newborn Infants. With Reference to a Simplified Micro-prothrombin Test," Am. J. Med. Sci., vol. 202:355-359 (1941).

Sah, Peter P.T., "Synthesis of 3-Methyl-4-Amino-1-naphthol hydrochloride (vitamin K) and related vitamin-K-active compounds," Zeitschrift fuer Vitamin-, Hormon- und Fermentforschung, vol. 3(3-4):324-345 (1949-1950).

Saltz, L. et al., "The presence and intensity of the cetuximab-induced acne-like rash predicts increased survival in studies across multiple malignancies," Proceedings of the American Society of Clinical Oncology, vol. 22, Abstr. No. 817 (2003).

Shah, Neha S. et al., "The effects of topical vitamin K on bruising after laser treatment," J. Am. Acad. Dermatol., vol. 47:241-244 (2002).

Soulieres, Denis et al., "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck," Journal of Clinical Oncology, vol. 22(1):77-85 (2004).

Susman, Ed, "Rash correlates with tumour response after cetuximab," The Lancet, Oncology, vol. 5:647 (2004).

Ulbrich, A.P., "Topical application of menadione, a synthetic vitamin K: Preliminary report," J. Am. Osteopathic Assoc., vol. 60:370-374 (1961).

Vanhoefer, Udo et al., "Phase I Study of the Humanized Antiepidermal Growth Factor Receptor Monoclonal Antibody EMD72000 in Patients With Advanced Solid Tumors That Express the Epidermal Growth Factor Receptor," J. Clin. Oncol., vol. 22:175-184 (2004).

* cited by examiner

Stage 1
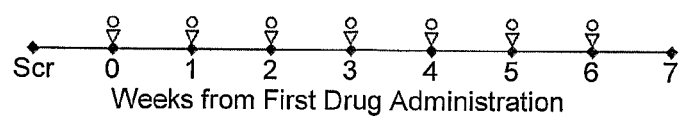
Weeks from First Drug Administration
Stage 2
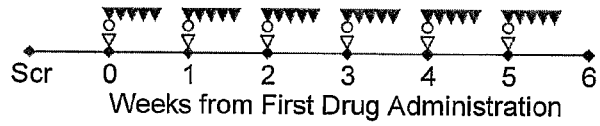
Weeks from First Drug Administration
◆ Visits
▽ Injection of anti-EGFr Ab
○ Injection of saline
▼ Injection of anti-IL8 Ab

SEQUENCE LISTING

```
<160> NUMBER OF SEQ ID NOS: 16

<210> SEQ ID NO 1
<211> LENGTH: 16
<212> TYPE: PRT
<213> ORGANISM: Homo sapiens

<400> SEQUENCE: 1

Asp Gly Ile Thr Met Val Arg Gly Val Met Lys Asp Tyr Phe Asp Tyr
1               5                   10                  15

<210> SEQ ID NO 2
<211> LENGTH: 8
<212> TYPE: PRT
<213> ORGANISM: Homo sapiens

<400> SEQUENCE: 2

Asp Arg Val Gly Leu Phe Asp Tyr
1               5

<210> SEQ ID NO 3
<211> LENGTH: 125
<212> TYPE: PRT
<213> ORGANISM: Homo sapiens

<400> SEQUENCE: 3

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
                100                 105                 110
```

```
Asp Tyr Trp Gly Gln Gly Thr Leu Val Thr Val Ser Ser
        115                 120                 125
```

```
<210> SEQ ID NO 4
<211> LENGTH: 107
<212> TYPE: PRT
<213> ORGANISM: Homo sapiens

<400> SEQUENCE: 4
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

```
<210> SEQ ID NO 5
<211> LENGTH: 5
<212> TYPE: PRT
<213> ORGANISM: Homo sapiens

<400> SEQUENCE: 5
```

```
Thr Tyr Gly Met His
1               5
```

```
<210> SEQ ID NO 6
<211> LENGTH: 17
<212> TYPE: PRT
<213> ORGANISM: Homo sapiens

<400> SEQUENCE: 6
```

```
Val Ile Trp Asp Asp Gly Ser Tyr Lys Tyr Tyr Gly Asp Ser Val Lys
1               5                   10                  15

Gly
```

```
<210> SEQ ID NO 7
<211> LENGTH: 11
<212> TYPE: PRT
<213> ORGANISM: Homo sapiens

<400> SEQUENCE: 7
```

```
Arg Ala Ser Gln Asp Ile Ser Ser Ala Leu Val
1               5                   10
```

```
<210> SEQ ID NO 8
<211> LENGTH: 7
<212> TYPE: PRT
<213> ORGANISM: Homo sapiens

<400> SEQUENCE: 8
```

```
Asp Ala Ser Ser Leu Glu Ser
1               5
```

```
<210> SEQ ID NO 9
<211> LENGTH: 9
<212> TYPE: PRT
<213> ORGANISM: Homo sapiens

<400> SEQUENCE: 9

Gln Gln Phe Asn Ser Tyr Pro Leu Thr
1               5

<210> SEQ ID NO 10
<211> LENGTH: 117
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser His Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Glu Tyr Asn Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser
        115

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Pro Gly Thr Lys Val Asp Ile Lys
            100                 105

<210> SEQ ID NO 12
<211> LENGTH: 5
<212> TYPE: PRT
<213> ORGANISM: Homo sapiens

<400> SEQUENCE: 12
```

```
His Tyr Gly Met Tyr
1               5

<210> SEQ ID NO 13
<211> LENGTH: 17
<212> TYPE: PRT
<213> ORGANISM: Homo sapiens

<400> SEQUENCE: 13

Val Ile Trp Tyr Asp Gly Ser Tyr Glu Tyr Asn Glu Asp Ser Val Lys
1               5                   10                  15
Gly

<210> SEQ ID NO 14
<211> LENGTH: 12
<212> TYPE: PRT
<213> ORGANISM: Homo sapiens

<400> SEQUENCE: 14

Arg Ala Ser Gln Ser Ile Ser Ser Ser Tyr Leu Ala
1               5                   10

<210> SEQ ID NO 15
<211> LENGTH: 7
<212> TYPE: PRT
<213> ORGANISM: Homo sapiens

<400> SEQUENCE: 15

Gly Pro Ser Ser Arg Ala Thr
1               5

<210> SEQ ID NO 16
<211> LENGTH: 8
<212> TYPE: PRT
<213> ORGANISM: Homo sapiens

<400> SEQUENCE: 16

Gln Gln Tyr Ala Gly Ser Leu Thr
1               5
```

METHOD OF TREATING RASH IN PATIENTS UNDERGOING ANTI-EGFR THERAPY

All patents, patent applications and other publications cited herein are hereby incorporated by reference in their entirety.

FIELD OF THE INVENTION

The present invention relates to methods and medicaments for reducing potential undesired dermatological side-effects of anti-epidermal growth factor receptor (EGFR) therapy, in particular the reduction of rash using IL8 inhibitors.

BACKGROUND OF THE INVENTION

Human EGFR is dysregulated in many solid tumors, making it an attractive target for anticancer therapy. A number of agents that target this receptor, including antibodies, are in use or in clinical development.

Interleukin-8 (IL8) is a chemokine belonging to the CXC group of chemokines. IL8 is a survival factor for a variety of cell types, including tumor cells. Combined administration of antibodies to IL8 and EGFR has been reported to result in increased antimetastatic effects on human breast carcinoma xenografts in mice (Salcedo et al. (2002) Clin. Cancer. Res. 8:2655-2665).

Undesired side-effects of anti-EGFR treatment include adverse gastrointestinal effects, such as diarrhea, and electrolyte abnormalities, in particular hypomagnesaemia. Other adverse effects common to anti-EGFR agents include undesired dermatological side-effects, such as papulopustolar rash, usually on the face, upper back and upper torso, which generally develops in a dose-dependent manner. Findings suggest that there is a relationship between the development of rash and response and/or survival. Although most patients only see mild to moderate skin toxicity, clinical benefit of increasing the dose of the various EGFR inhibitors is expected.

Histological data indicate that rash is caused directly by EGFR inhibition in skin. Serial biopsies of skin before and after treatment revealed two main reaction patterns: a superficial dermal inflammatory cell infiltrate surrounding hyperkeratotic and ectatic follicular infundibula, and a suppurative superficial folliculitis. Follicular accumulation of neutrophilic granulocytes is considered characteristic for the skin lesion observed after EGFR inhibition. Otherwise, however, little is known about the etiology of this rash, and there are no clear evidence-based management recommendations.

SUMMARY OF THE INVENTION

The present invention relates to the use of anti-neutrophil-chemoattractant agents, in particular IL8 inhibitors, for the reduction of undesired dermatological side-effects of EGFR treatment, in particular the reduction of rash.

Without being bound by one specific theory, it is believed that neutrophils may at least be partly responsible for the observed tissue damages occurring at the inflammatory site, and that inhibition of a neutrophil chemoattractant agent may reduce or even prevent massive accumulation of active neutrophils in skin lesion areas, thus reducing the occurrence of rash.

Furthermore, a clinical benefit of managing the skin lesions is expected to allow a better response and/or survival of EGFR inhibition treated cancer as the dose or duration of treatment with EGFR inhibitor could be increased.

Accordingly, in a first main aspect, the invention relates to a method for the treatment of a disease susceptible to anti-EGFR treatment, comprising the step of administering, to a human being in need thereof, a combination of an anti-EGFR agent and an anti-neutrophil-chemoattractant agent, wherein said anti-neutrophil-chemoattractant agent is administered in a dosage regimen that is sufficient to reduce one or more undesired dermatological side-effects of the anti-EGFR agent.

Similarly, the invention relates to the use of a combination of an anti-EGFR agent with an anti-neutrophil-chemoattractant agent for the preparation of a medicament for the treatment of a disease susceptible to anti-EGFR treatment, wherein said anti-neutrophil-chemoattractant agent is present in a dose sufficient to reduce one or more undesired dermatological side-effects of EGFR treatment.

In another aspect, the invention relates to a method for reducing undesired dermatological side-effects in an individual who is undergoing, or is enrolled to undergo anti-EGFR treatment, said method comprising the step of administering anti-neutrophil-chemoattractant agent to said individual.

Similarly, the invention relates to the use of an anti-neutrophil-chemoattractant agent for the preparation of a medicament for reducing an undesired dermatological side-effect in an individual undergoing, or enrolled to undergo, anti-EGFR treatment.

In a further aspect, the invention relates to a composition suitable for use in the method of the invention, comprising an anti-EGFR agent and an anti-neutrophil-chemoattractant agent, wherein said anti-neutrophil-chemoattractant agent is present in an amount sufficient to reduce one or more undesired dermatological side-effects of the anti-EGFR agent.

In an even further aspect, the invention relates to a kit of parts for use in the methods of the invention, comprising, (i) a formulation comprising an anti-EGFR agent in admixture with a pharmaceutically acceptable adjuvant, diluent, or carrier; and (ii) a formulation comprising an anti-neutrophil-chemoattractant agent in an amount sufficient to reduce one or more undesired dermatological side-effects of the anti-EGFR agent in admixture with a pharmaceutically acceptable adjuvant, diluent, or carrier, wherein agents (i) and (ii) are each formulated for administration in conjunction with the other.

BRIEF DESCRIPTION OF THE FIGURE

FIG. 1 gives an overview the treatment protocol described in Example 1.

DETAILED DESCRIPTION OF THE INVENTION

Definitions

When used herein, the term "disease susceptible to anti-EGFR treatment" refers to any disease or condition that can be cured or ameliorated by treatment with an anti-EGFR agent.

As used herein, the term "anti-X agent" refers to an agent, i.e. a molecule, capable of inhibiting the biological function of X. Thus, an "anti-EGFR agent" refers to a molecule capable of inhibiting EGFR function. An "anti-neutrophil-chemoattractant agent" refers to a molecule capable of inhibiting the function of a neutrophil-chemoattractant, such as IL8. Typically, the anti-X agent is a binding molecule which e.g. inhibits or blocks binding of a ligand to a receptor. E.g. an anti-EGFR agent can be a binding molecule, such as an antibody, which inhibits binding of a ligand to EGFR. An anti-neutrophil-chemoattractant agent can be a molecule, e.g. an antibody, which binds a neutrophil-chemoattractant, such as IL8, and inhibits its biological activity, e.g. inhibits its binding to its receptor.

As used herein, the terms "inhibits binding" and "blocks binding" (for instance when referring to inhibition/blocking of binding of a ligand to EGFR or of binding of IL8 to a receptor) are used interchangeably herein and encompass both partial and complete inhibition/blocking. The inhibition/blocking of binding of a ligand to a receptor normally reduces or alters the normal level or type of cell signaling that occurs when a ligand binds to the receptor. Inhibition and blocking are also intended to include any measurable decrease in the binding affinity of a ligand to its receptor due to a binding protein, e.g. an antibody. Binding of a ligand to a receptor may e.g. be inhibited by at least about 10%, 20%, 30%, 40%, 50%, 60%, 70%, 80%, 90%, 99%, or 100%.

When used herein, the term "undesired side-effect" refers to an unintended adverse event associated with the treatment of a subject with a medicament.

When used herein, the term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions may be further subdivided into regions of hyper-variability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions for significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation.

As indicated above, the term antibody herein, unless otherwise stated or clearly contradicted by context, includes fragments of an antibody that retain the ability to specifically bind to an antigen. It has been shown that the antigen-binding function of an antibody may be performed by fragments of a full-length antibody. Examples of binding fragments encompassed within the term "antibody" include, but are not limited to: (i) a Fab fragment, a monovalent fragment consisting of the $V_L$, $V_H$, $C_L$ and $C_H1$ domains; (ii) $F(ab)_2$ and $F(ab')_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol 2003 November; 21(11):484-90); (vi) camelid or nanobodies (Revets et al; Expert Opin Biol Ther. 2005 January; 5(1):111-24), and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context.

Antibodies interact with target antigens primarily through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted into framework sequences from a different antibody with different properties (see for instance Riechmann, L. et al., Nature 332, 323-327 (1998), Jones, P. et al., Nature 321, 522-525 (1986) and Queen, C. et al., PNAS USA 86, 10029-10033 (1989)).

It also should be understood that the term antibody also generally includes polyclonal antibodies, monoclonal antibodies (mAbs), antibody-like polypeptides, such as chimeric antibodies and humanized antibodies, anti-idiotypic (anti-Id) antibodies to antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell. The term "multispecific molecule" is intended to include any agent, for instance a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. The term "bispecific antibodies" is intended to include any anti-EGFR or anti-IL8 antibody, which is a bispecific molecule. The term "bispecific antibodies" also includes diabodies.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, neutrophils, polymorphonuclear cells, granulocytes, mast cells, and basophiles. Some effector cells express specific Fc receptors and carry out specific immune functions. In some embodiments, an effector cell is capable of inducing antibody-dependent cellular cytotoxicity (ADCC), such as a neutrophil capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen, target cell, or microorganism. The expression of a particular FcR on an effector cell may be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

The term "human antibody", as used herein, is intended to include antibodies having variable and constant regions derived from human germline immunoglobulin sequences. The human antibodies of the present invention may include amino acid residues not encoded by human germ line immunoglobulin sequences (for instance mutations introduced by random or site-specific mutagenesis in vitro or by somatic mutation in vivo). However, the term "human antibody", as used herein, is not intended to include antibodies in which CDR sequences derived from the germ line of another mammalian species, such as a mouse, have been grafted into human framework sequences. As used herein, a human antibody is "derived from" a particular germ line sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germ line immunoglobulin gene. Typically, outside the heavy chain CDR3, a human antibody derived from a particular human germ line sequence will display no more than 10 amino acid differences, such as no more than 5, for instance no more than 4, 3, 2, or 1 amino acid difference from the amino acid sequence encoded by the germ line immunoglobulin gene.

The term "chimeric antibody" refers to an antibody that contains one or more regions from one antibody and one or more regions from one or more other antibodies. The term "chimeric antibody" includes monovalent, divalent, or polyvalent antibodies. Chimeric antibodies are produced by recombinant processes well known in the art (see for instance Cabilly et al, PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A "humanized antibody" is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody typically also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germ line immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared there from (described further elsewhere herein), (b) antibodies isolated from a host cell transformed to express the antibody, such as from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germ line immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

As used herein, "antibody capable of binding X" refers to the binding of an antibody to a predetermined antigen X. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low, then the amount with which the affinity for the antigen is lower than the affinity for a non-specific antigen may be at least 10,000 fold. Binding affinity also may be determined by equilibrium methods (for instance enzyme-linked immunoabsorbent assay (ELISA) or radioimmunoassay (RIA)).

The term "$k_d$" (sec$^{-1}$), as used herein, refers to the dissociation equilibrium rate constant of a particular antibody-antigen interaction. Said value is also referred to as the $K_{off}$ value.

The term "$k_a$" (M$^{-1}$×sec$^{-1}$), as used herein, refers to the association equilibrium rate constant of a particular antibody-antigen interaction.

The term "$K_D$" (M), as used herein, refers to the dissociation equilibrium constant of a particular antibody-antigen interaction.

The term "$K_A$" (M$^{-1}$), as used herein, refers to the association equilibrium constant of a particular antibody-antigen interaction and is obtained by dividing the $k_a$ by the $k_d$.

Antigen binding is preferably specific. The term "specific" herein refers to the ability of an antibody, e.g. an anti-EGFR antibody or anti-IL8 antibody, to recognize an epitope within an antigen, e.g. EGFR or IL8, while only having little or no detectable reactivity with other portions of the antigen or with another, unrelated, antigen. Specificity may be relatively determined by competition assays as described herein. Specificity can more particularly be determined by any of the epitope identification/characterization techniques described herein or their equivalents known in the art. An antibody specific for a particular antigenic determinant may nonetheless cross-react with other biomolecules. For instance, an anti-EGFR antibody that binds human EGFR may cross-react with EGFR homologues from other species.

As used herein, "isotype" refers to the immunoglobulin class (for instance IgG1, IgG2, IgG3, IgG4, IgD, IgA, IgE, or IgM) that is encoded by heavy chain constant region genes.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-EGFR antibodies when immunized with human EGFR antigen and/or cells expressing EGFR. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The antibodies used in the present invention are typically used in and provided in an at least substantially isolated form. An "isolated" molecule refers to a molecule that is not associated with significant levels (such as more than about 1%, more than about 2%, more than about 3%, or more than about 5%) of any extraneous and undesirable physiological factors, such as non-EGFR or IL8 binding biomolecules contained within a cell or animal in which the antibody is produced. An isolated molecule also refers to any molecule that has passed through such a stage of purity due to human intervention (whether automatic, manual, or both).

"Treatment" means the administration of an effective amount of a therapeutically active compound of the present invention with the purpose of easing, ameliorating, or eradicating (curing) symptoms or disease states.

EMBODIMENTS OF THE INVENTION

In a first main aspect, the invention relates to a method for the treatment of a disease susceptible to anti-EGFR treatment, comprising the step of administering, to a human being in need thereof, a combination of an anti-EGFR agent and an anti-neutrophil-chemoattractant agent, wherein said anti-neutrophil-chemoattractant agent is administered in a dosage regimen that is sufficient to reduce one or more undesired dermatological side-effects of the anti-EGFR agent.

Similarly, the invention relates to the use of a combination of an anti-EGFR agent with an anti-neutrophil-chemoattractant agent for the preparation of a medicament for the treatment of a disease susceptible to anti-EGFR treatment, wherein said anti-neutrophil-chemoattractant agent is present in a dose sufficient to reduce one or more undesired dermatological side-effects of EGFR treatment. The agents may be administered from different vials or from one and the same solution.

In another aspect, the invention relates to a method for reducing undesired dermatological side-effects in an individual who is undergoing, or is enrolled to undergo anti-EGFR treatment, said method comprising the step of administering anti-neutrophil-chemoattractant agent to said individual.

Similarly, the invention relates to the use of an anti-neutrophil-chemoattractant agent for the preparation of a medicament for reducing an undesired dermatological side-effect in an individual undergoing, or enrolled to undergo, anti-EGFR treatment.

Diseases Susceptible to Anti-EGFR Treatment

In one embodiment of the method or use of the invention, the disease susceptible to anti-EGFR treatment is cancer.

In one embodiment, said cancer is selected from the group consisting of: breast cancer, bladder cancer, uterine/cervical cancer, esophageal cancer, pancreatic cancer, colon cancer, colorectal cancer, kidney cancer, ovarian cancer, prostate cancer, renal cancer, head and neck cancer (SCCHN), non-small cell lung cancer (NSCLC) and stomach cancer. In a preferred embodiment, said cancer is head and neck cancer or non-small cell lung cancer. In another embodiment, said cancer is selected from the group consisting of: bladder cancer, uterine/cervical cancer, esophageal cancer, pancreatic cancer, colorectal cancer, kidney cancer, ovarian cancer, prostate cancer, head and neck cancer, non-small cell lung cancer and stomach cancer. In an even further embodiment, said cancer is not breast cancer.

In another embodiment, the disease susceptible to anti-EGFR treatment is selected from the group consisting of psoriasis, rheumatoid arthritis, systemic lupus erythematosus, psoriatic arthritis, Menetrier's disease, systemic sclerosis, Sjögren's syndrome, pulmonary fibrosis, bronchial asthma, myelofibrosis, diabetic nephropathy, chronic allograft rejection, chronic glomerulonephritis, Crohn's disease, ulcerative colitis, hepatic cirrhosis, sclerosing cholangitis, chronic uveitis, cicatricial pemphigoid and chronic obstructive pulmonary disease (COPD).

In a preferred embodiment, the disease susceptible to anti-EGFR treatment is selected from the group consisting of Menetrier's disease, systemic sclerosis, Sjögren's syndrome, pulmonary fibrosis, bronchial asthma, myelofibrosis, diabetic nephropathy, chronic allograft rejection, chronic glomerulonephritis, Crohn's disease, ulcerative colitis, hepatic cirrhosis, sclerosing cholangitis, chronic uveitis, and cicatricial pemphigoid.

In a further embodiment, the disease susceptible to anti-EGFR treatment is Alzheimer's disease or other forms of dementia.

In a yet further embodiment, the disease susceptible to anti-EGFR treatment is human cytomegalovirus (HCMV) infection, such as HCMV infection in connection with HIV/AIDS or following organ transplantation.

In an even further embodiment, embodiment, the disease susceptible to anti-EGFR treatment is selected from glioblastoma, including glioblastoma multiforme astrocytoma, including childhood astrocytoma; glioma; neuroblastoma; *Helicobacter pylori* infection, including *Helicobacter pylori* infection associated with gastric mucosa associated lymphoid tissue (MALT) lymphoma; neuroendocrine tumors of the gastrointestinal tract; bronchoalveolar carcinoma; follicular dendritic cell sarcoma; salivary gland carcinoma; ameloblastoma; malignant peripheral nerve sheet tumor; endocrine pancreatic tumors; testicular germ cell tumors, including seminoma, embryonal carcinoma, yolk sac tumor, teratoma and choriocarcinoma; chronic sinusitis; allergic rhinitis; glaucoma, including glaucomatous optic neuropathy; cardiac hypertrophy; injury-induced arterial intimal hyperplasia; and ischaemia-reperfusion injury.

In one embodiment of the method of the invention, the human being who is being treated is a human being susceptible to developing rash when subjected to anti-EGFR treatment.

In another embodiment of the method of the invention, the human being who is being treated is a human being who has been diagnosed for exhibiting an undesired dermatological side-effect, such as rash.

Anti-EGFR Agents

In one embodiment of the method of the invention, the anti-EGFR agent used is a tyrosine kinase inhibitor. Examples of suitable tyrosine kinase inhibitors are the quinazoline derivatives described in WO 96/33980, in particular gefitinib (Iressa). Other examples include quinazoline derivatives described in WO 96/30347, in particular erlotinib (Tarceva), dual EGFR/HER2 tyrosine kinase inhibitors, such as lapatinib, or pan-Erb inhibitors.

In a preferred embodiment of the method or use of the invention, the anti-EGFR agent is an antibody capable of binding to EGFR, i.e. an anti-EGFR antibody.

In one embodiment, the anti-EGFR antibody is a humanized antibody. In another embodiment, the anti-EGFR antibody is a chimeric antibody. In another embodiment, the anti-EGFR antibody is a human antibody. In a further embodiment, the anti-EGFR antibody is a polyclonal antibody. In a yet further embodiment, the anti-EGFR antibody is a monoclonal antibody. In an even further embodiment, the anti-EGFR antibody is a human monoclonal antibody.

In a further preferred embodiment, the anti-EGFR antibody is an intact antibody, i.e. a full-length antibody rather than a fragment.

An anti-EGFR antibody used in the method of the present invention may have any suitable affinity and/or avidity for one or more epitopes contained at least partially in EGFR. Preferably, the antibody used binds to human EGFR with an equilibrium dissociation constant ($K_D$) of $10^{-8}$ M or less, more preferably $10^{-10}$ M or less.

In a preferred embodiment, the anti-EGFR antibody used is an antibody as described in WO02/100348, WO04/056847, WO200556606, WO05/012479, WO05/10151, U.S. Pat. No. 6,794,494, EP1454917, WO0314159, WO02092771, WO0312072, WO02066058, WO0188138, WO98/50433, WO98/36074, WO96/40210, WO 96/27010, US2002065398, WO95/20045, EP586002, U.S. Pat. No. 5,459,061 or U.S. Pat. No. 4,943,533.

Particularly preferred antibodies for use in the present invention include zalutumumab (2F8, described in WO02/100348 and WO04/056847), cetuximab (Erbitux), nimotuzumab (h-R3), panitumumab (ABX-EGF), and matuzumab (EMD72000), or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Thus, in one preferred embodiment, the present invention uses anti-EGFR antibody 2F8 or a variant thereof or an antibody which is able to compete with 2F8, such as an antibody recognizing the same epitope as 2F8. The heavy and light chain variable region sequences of 2F8 are set forth in SEQ ID NOs: 3 and 4, respectively; the heavy chain CDR 1 and CDR2 regions are set forth in SEQ ID NOs: 5 and 6, respectively; and the light chain CDR 1, CDR2, and CDR3 regions are set forth in SEQ ID NOs: 7, 8, and 9, respectively. Preferred variant antibodies include antibodies comprising the same heavy chain CDR3 sequence as 2F8, i.e. the CDR3 sequence set forth in SEQ ID NO:1. Other preferred variant antibodies are antibodies having a variant region which is at least 70%, such as at least 80%, e.g., at least 90%, such as at least 95%, e.g. at least 98% or at least 99% identical to the variable region of 2F8(WO 02/100348).

Further preferred anti-EGFR antibodies for use in the invention comprise antibodies that have one or more of the following properties:
a) the ability to opsonize a cell expressing EGFR;
b) the ability to inhibit growth and/or mediate phagocytosis and killing of cells expressing EGFR (e.g., a tumor cell) in the presence of human effector cells at a concentration of about 10 μg/ml or less (e.g., in vitro).

Anti-EGFR antibodies used in the present invention may be in any suitable form with respect to multimerization. Also, if desired, the class of anti-EGFR antibody used in the present invention may be switched by known methods. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment, the anti-EGFR antibody used in the present invention is an IgG1 antibody, for instance an IgG1,κ or IgG1,λ isotype. In another embodiment, the anti-EGFR antibody used in the present invention is an IgG3 antibody, for instance an IgG3,κ or IgG3,λ isotype. In yet another embodiment, the antibody used is an IgG4 antibody, for instance an IgG4,κ or IgG4,λ isotype. In a further embodiment, the anti-EGFR antibody used in the present invention is an IgA1 or IgA2 antibody. In an even further embodiment, the anti-EGFR antibody used in the present invention is an IgM antibody.

Further possible embodiments of the anti-EGFR antibody used in the present invention are given below in the section "Production of antibodies".

Anti-Neutrophil-Chemoattractant Agents

In one embodiment of the method of the invention, the anti-neutrophil-chemoattractant agent is selected from the group of: an anti-Groα (CXCL1) agent, an anti-Groβ (CXCL2) agent, an anti-Groγ (CXCL3) agent, an anti-ENA-78 (CXCL5) agent, an anti-GCP-2 (CXCL6) agent, an anti-NAP-2 (CXCL7) agent, and an anti-IL8 (CXCL8) agent. For reference, see Roitt Essential Immunology 10th Ed. 2001 Blackwell Publishing.

In a particularly preferred embodiment of the method or use of the invention, the anti-neutrophil-chemoattractant agent used is an anti-IL8 agent. In a more preferred embodiment, the anti-IL8 agent is an antibody capable of binding to IL8, i.e. an anti-IL8 antibody.

In one embodiment, the anti-IL8 antibody is a humanized antibody. In another embodiment, the anti-IL8 antibody is a chimeric antibody. In a further embodiment, the anti-IL8 antibody is a human antibody. In another embodiment, the anti-IL8 antibody is a polyclonal antibody. In a yet other embodiment, the anti-IL8 antibody is a monoclonal antibody. In an even further embodiment, the anti-IL8 antibody is a human monoclonal antibody.

In a further preferred embodiment, the anti-IL8 antibody is an intact antibody, i.e. a full-length antibody rather than a fragment.

An anti-IL8 antibody used in the method of the present invention may have any suitable affinity and/or avidity for one or more epitopes contained at least partially in IL8. Preferably, the antibody used binds to human IL8 with an equilibrium dissociation constant ($K_D$) of $10^{-8}$ M or less, more preferably $10^{-10}$ M or less.

In a preferred embodiment, the anti-IL8 antibody used is an antibody as described in WO04/058797 (Genmab/Medarex), WO02/072788 (Centocor), WO98/037200 (Genentech), WO99/037779 (Genentech), U.S. Pat. No. 6,025,158 (Genentech), U.S. Pat. No. 6,117,980 (Genentech), U.S. Pat. No. 6,133,426 (Genentech), WO92/04372 (Scripps Research Institute), U.S. Pat. No. 5,831,032 (Scripps Research Institute), WO91/10741, WO94/02602, WO96/33735, WO98/24893 (Abgenix), U.S. Pat. No. 5,939,598, 6,075,181, 6,114,598, 6,150,584, 6,162,963, 6,657,103, 6,673,986, 6,713,610 (Abgenix), WO89/08665, U.S. Pat. No. 5,698,196 , 6,376,659, or U.S. Pat. No. 6,475,741 (National Institute of Health).

In a particularly preferred embodiment, the antibody used in the present invention is ABX-IL8 (Huang et al (2002) Am. J. Pathol 161:125-134) or 10F8 (described in WO2004058797) or a variant antibody of any of these, or an antibody which is able to compete with any of these, such as an antibody recognizing the same epitope as any of these. Competition may be determined by any suitable technique. In one embodiment, competition is determined by an ELISA assay. Often competition is marked by a significantly greater relative inhibition than 5% as determined by ELISA analysis.

Thus, in one preferred embodiment, the present invention uses anti-IL8 antibody 10F8 or a variant thereof or an antibody which is able to compete with 10F8, such as an antibody recognizing the same epitope as 10F8. The heavy and light chain variable region sequences of 10F8 are set forth in SEQ ID NOs: 10 and 11, respectively; the heavy chain CDR 1 and CDR2 regions are set forth in SEQ ID NOs: 12 and 13, respectively; and the light chain CDR 1, CDR2, and CDR3 regions are set forth in SEQ ID NOs: 14, 15, and 16, respectively. Preferred variant antibodies include antibodies comprising the same heavy chain CDR3 sequence as 10F8, i.e. the CDR3 sequence set forth in SEQ ID NO:2. Other preferred variant antibodies are antibodies having a variant region which is at least 70%, such as at least 80%, e.g., at least 90%, such as at least 95%, e.g. at least 98% or at least 99% identical to the variable region of 10F8.

Anti-IL8 antibodies used in the present invention may be in any suitable form with respect to multimerization. Also, if desired, the class of anti-IL8 antibody used in the present invention may be switched by known methods. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment, the anti-IL8 antibody used in the present invention is an IgG1 antibody, for instance an IgG1,κ or IgG1,λ isotype. In another embodiment, the anti-IL8 antibody used in the present invention is an IgG3 antibody, for instance an IgG3,κ or IgG3,λ isotype. In yet another embodiment, the antibody used is an IgG4 antibody, for instance an IgG4,κ or IgG4,λ isotype. In a further embodiment, the anti-IL8 antibody used in the present invention is an IgA1 or IgA2 antibody. In an even further embodiment, the anti-IL8 antibody used in the present invention is an IgM antibody.

Further possible embodiments of the anti-IL8 antibody used in the present invention are given below in the section "Production of antibodies".

Production of Antibodies

A monoclonal antibody refers to a composition comprising a homogeneous antibody population having a uniform structure and specificity. That an antibody is monoclonal is not to be construed as requiring production of the antibody by any particular method. For example, the monoclonal antibodies used in the present invention may be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991).

Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc. In one embodiment, human monoclonal antibodies directed against EGFR or IL8 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424). In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478. Splenocytes from these transgenic mice may be used to generate hybridomas that secrete human monoclonal antibodies according to well known techniques.

Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, 5,756,687, 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized, for instance as described elsewhere herein.

Anti-EGFR antibodies and/or anti-neutrophil-chemoattractant antibodies may be recovered from recombinant combinatorial antibody libraries, such as a scFv phage display library, which may be made with human $V_L$ and $V_H$ cDNAs prepared from mRNA derived from human lymphocytes. Methods for preparing and screening such libraries are known in the art.

A "variant" antibody is an antibody that differs from a parent antibody (typically generated by immunization) by one or more suitable amino acid residue alterations, that is substitutions, deletions, insertions, or terminal sequence additions, in the CDRs or other $V_H$ and/or $V_L$ sequences (provided that at least a substantial amount of the epitope binding characteristics of the parent antibody are retained, if not improved upon, by such changes). Variations in an antibody variant may be made in each of the framework regions, the constant domain, and/or the variable regions (or any one or more CDRs thereof) in a single variant antibody. Alternatively, variations may be made in only one of the framework regions, the variable regions (or single CDR thereof), or the constant domain in an antibody.

A suitable amino acid residue substitution in the context of a CDR variant is any amino acid residue that permits the CDR to interact with the epitope to which the parent CDR is selective/specific and to cooperatively associate with other parent CDRs and/or variant CDRs similarly specific/selective for that epitope. Factors influencing the selection of a suitable amino acid sequence substitution may include the impact of the residue on the conformation of the CDR (e.g., retention of CDR loop structure and flexibility) and the ability to engage in noncovalent interactions (e.g., Van der Waals interactions, hydrogen bonding interactions, ionic interactions, and/or other interactions characteristic of epitope-variable region binding) with the epitope and/or other similar CDRs in a manner similar to or advantageous over the replaced residue in the parent CDR.

The percent identity between two sequences, e.g. variable domain sequences or CDR3 sequences, is a function of the number of identical positions shared by the sequences (i.e., % homology=# of identical positions/total # of positions× 100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

Amino acid residue classes for conservative substitutions

| Acidic Residues | Asp and Glu |
| Basic Residues | Lys, Arg, and His |
| Hydrophilic Uncharged Residues | Ser, Thr, Asn, and Gln |
| Aliphatic Uncharged Residues | Gly, Ala, Val, Leu, and Ile |
| Non-polar Uncharged Residues | Cys, Met, and Pro |
| Aromatic Residues | Phe, Tyr, and Trp |

Variant anti-EGFR or anti-IL8 antibodies used in the present invention may comprise framework (FR) alterations, that is outside the hypervariable region, for instance in the Fc region, which alterations may be associated with advantageous properties, such as changing the functional or pharmacokinetic properties of the antibodies. For example, a substitution or other modification (insertion, deletion, terminal sequence additions or combination of any thereof) in a framework region or constant domain may be associated with an increase in the half-life of the variant antibody with respect to the parent antibody, or may be made to alter the immunogenicity of the variant antibody with respect to the parent antibody, to provide a site for covalent or non-covalent binding to another molecule, or to alter such properties as complement fixation, for instance resulting in a decrease or increase of C1q binding and CDC or of FcγR binding and antibody-dependent cellular cytotoxicity (ADCC). Substitutions may for example be made in one or more of the amino acid residues 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the $C_H2$ domain that alter the ability of the antibodies to bind to FcRI and thereby decreases the ability of the antibodies to bind to C1q which in turn decreases the ability of the antibodies to fix complement. Furthermore, Shields et al., J. Biol. Chem. 276, 6591-6604 (2001) teaches combination variants, which improve FcγRIII binding, for instance T256A/S298A, S298A/E333A, and S298A/E333A/K334A.

The in vivo half-life of the antibodies may also be improved by modifying the salvage receptor epitope of the Ig constant domain or an Ig-like constant domain such that the molecule does not comprise an intact $C_H2$ domain or an intact Ig Fc region, cf. U.S. Pat. No. 6,121,022 and U.S. Pat. No. 6,194,551. The in vivo half-life may furthermore be increased by making mutations in the Fc region, e.g. by substituting threonine for leucine at position 252, threonine for serine at position 254, or threonine for phenylalanine at position 256, cf. U.S. Pat. No. 6,277,375.

The present invention may also use fragments of antibodies (including variant antibodies). Examples of such antibody fragments include Fab, Fab', F(ab')$_2$, and Fv fragments. Thus, although the discussion herein may focus on antibodies, it should be understood that the embodiments and features of the antibodies may equally be applied to antibody fragments, such as Fab fragments, Fab' fragments, and scFv peptides, antibody-like peptides (peptides comprising a CDR), and bi- and multi-specific antibodies as appropriate, provided that the molecule retains at least a substantial proportion of the antigen-binding properties of the corresponding complete antibody. In some instances, antibody fragments may be associated with lower antigen-binding affinity, but may offer other advantageous features that may offset for any such loss in affinity.

Antibodies used in the present invention also include antibody derivatives. Such derivatives may be produced by chemically conjugating a radioisotope, protein, or other agent/moiety/compound to the N-terminal side or C-terminal side of the antibody or subunit thereof, an appropriate substituent group or side chain or to a sugar chain in the antibody (see, e.g., Antibody Engineering Handbook, edited by Osamu Kanemitsu, published by Chijin Shokan (1994)). Derivatives may also be generated by conjugation at internal residues or sugars, where appropriate.

In one embodiment, the present invention uses an anti-EGFR antibody that is conjugated to a second molecule that is selected from a radionuclide, an enzyme, an enzyme substrate, a cofactor, a fluorescent marker, a chemiluminescent marker, a peptide tag, or a magnetic particle. In one embodiment, an anti-EGFR antibody may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to an anti-EGFR antibody and/or anti-IL8 antibody. One example of indirect coupling of a second agent is coupling by a spacer moiety. These spacers, in turn, may be either insoluble or soluble (see for instance Diener et al, Science 231, 148 (1986)) and may be selected to enable drug release from the antibody at a target site and/or under particular conditions. Additional examples of therapeutic agents that may be coupled to an anti-EGFR antibody and/or anti-IL8 antibody include lectins and fluorescent peptides.

In one embodiment, anti-EGFR antibody derivatives comprising one or more radiolabeled amino acids are used. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, 4,735,210, 5,101,827, 5,102,990 (U.S. RE35,500), U.S. Pat. No. 5,648, 471 and U.S. Pat. No. 5,697,902. For example, a radioisotope may be conjugated by a chloramine T method.

In one embodiment, the present invention provides cross-linked anti-EGFR antibody and/or anti-IL8 antibody derivatives. For example, such a derivative may be produced by crosslinking two or more antibodies, at least one of which is specific/selective for EGFR or IL8 (of the same type or of different types, e.g., to create bispecific antibodies). Suitable crosslinkers include those that are heterobifunctional, having two distinctly reactive groups separated by an appropriate spacer (e.g., m-male-imidobenzoyl-N-hydroxysuccinimide ester) or homobifunctional (e.g., disuccinimidyl suberate). Such linkers are available from Pierce Chemical Company, Rockford, Ill.

In one embodiment, the present invention uses molecules comprising an anti-EGFR antibody, such as a human an anti-EGFR antibody, conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins. Therapeutic agents, which may be administered in combination with an anti-EGFR antibody and/or anti-IL8 antibody as described elsewhere herein, may also be candidates for therapeutic moieties useful for conjugation to an anti-EGFR antibody and/or anti-IL8 antibody.

Other examples of therapeutic cytotoxins that may be conjugated to an anti-EGFR antibody and/or anti-IL8 antibody used in the present invention include calicheamicins and duocarmycins. As indicated above, the drug moiety need not be construed as limited to classical chemical therapeutic agents. For example, the drug moiety may be a protein or polypeptide possessing a desired biological activity. Such proteins may include, for example, an agent active at the cell surface, such as phospholipase enzymes, e.g. phospholipase C.

The lysing portion of a toxin typically may be readily joined to the Fab fragment of an antibody or antibody fragment of the present invention. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Additional toxins suitable for use in the present invention are known to those of skill in the art (see for instance U.S. Pat. No. 6,077,499).

Techniques for conjugating such therapeutic moieties to antibodies, are well known, see for instance Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985), Hellstrom et al., "Antibodies For Drug Delivery", in Controlled Drug Delivery (2nd Ed.), Robinson et al., (eds.), pp. 623-53 (Marcel Dekker, Inc. 1987), Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985), "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985) and Thorpe et al., "The Preparation And Cytotoxic Properties Of Antibody-Toxin Conjugates", Immunol. Rev. 62, 119-58 (1982).

In one embodiment, the anti-EGFR antibody and/or anti-IL8 antibody used in the present invention is attached to a linker-chelator, e.g., tiuxetan, which allows for the antibody to be conjugated to a radioisotope.

Additionally useful conjugate substituents include anticancer retinoids. Taxane conjugates (see for instance Jaime et al., Anticancer Res. 21(2A), 1119-28 (2001), cisplatin conjugates, thapsigargin conjugates, linoleic acid conjugates, calicheamicin conjugates (see for instance Damle et al., Curr Opin Pharmacol. 3(4), 386-90 (2003), doxorubicin conjugates, geldanamycin conjugates, and the like, also may be useful in promoting the treatment of cancer (see, generally, Trail et al., Cancer Immunol Immunother. 52(5), 328-37 (2003)).

Antibodies used in the present invention may be prepared by recombinant expression in any suitable type of cells or animals. Recombinant antibodies, such as recombinant human antibodies also include antibodies isolated from a recombinant, combinatorial human antibody library, antibodies isolated from an animal, such as a transgenic animal, or antibodies prepared, expressed, created or isolated by any other means that involves splicing of human immunoglobulin-encoding nucleic acid sequences to other nucleic acid sequences exogenous to the human immunoglobulin-encoding nucleic acids and human immunoglobulin-encoding genes. Recombinant human antibodies typically have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and, thus, the amino acid sequences of the $V_H$ and $V_L$ regions of the recombinant antibodies may be sequences that, while derived from and related to human germ line $V_H$ and $V_L$ sequences, may not naturally exist within the human antibody germ line repertoire in vivo. Suitable methods for antibody production are known in the art and include those described in for instance Harlow et al., Antibodies: A Laboratory Manual, Cold Spring Harbor Laboratory Press, Cold Spring Harbor, N.Y., (1988), Harlow and Lane: Using Antibodies: A Laboratory Manual (Cold Spring Harbor Laboratory Press (1999)), U.S. Pat. No. 4,376,110 and Ausubel et al., eds., Current Protocols In Molecular Biology, Greene Publishing Assoc. and Wiley InterScience N.Y., (1987, 1992). Monoclonal antibodies may be made using the hybridoma method first described by Kohler et al., Nature 256, 495 (1975), or by other well-known, subsequently-developed methods (see, e.g., Goding, Monoclonal Antibodies: Principles and Practice, pp. 59-103 (Academic Press, 1986)). Transformed immortalized B cells may also be used to efficiently produce antibodies used in the present invention. Such cells may be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al., in Monoclonal Antibodies, ed. by Kennett R. H. et al, Plenum Press, N.Y. 1980, pp 19-33.).

Recombinant cells comprising exogenous nucleic acids encoding antibodies used in the present invention may be prepared by any suitable technique (e.g., transfection/transformation with a naked DNA plasmid vector, viral vector, invasive bacterial cell vector or other whole cell vector, etc., comprising an antibody-encoding sequence (or sequences) delivered into the cell by calcium phosphate-precipitation facilitated transfection, receptor-mediated targeting and transfection, biolistic delivery, electroporation, dextran-mediated transfection, liposome-mediated transformation, protoplast fusion, direct microinjection, etc.). Methods of transforming/transfecting cells are well known in the art (see, e.g., Sambrook et al., Molecular Cloning: A Laboratory Manual, Cold Spring Harbor Laboratory Press (2d Edition, 1989 and 3rd Edition, 2001) and F. Ausubel et al., ed. Current Protocols in Molecular Biology, Greene Publishing and Wiley InterScience New York (1987). Such recombinant cells are a feature of the present invention.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells., or bacterial cells or eukaryotic unicellular microorganisms, such as yeast.

Human antibodies of the present invention may also be produced in a host cell transfectoma using, for example, a combination of recombinant DNA techniques and gene transfection methods as is well known in the art, see for instance Morrison, S., Science 229, 1202 (1985).

Undesired Side-Effects

The undesired side-effect(s) or adverse effect(s) of anti-EGFR treatment that are reduced by administration of the anti-neutrophil chemoattractant agent, may be any type of dermatological side-effect of such treatment, such as rash, dry skin or nail changes, e.g. paronycia. However, in a preferred embodiment, the undesired dermatological side-effect that is reduced by the anti-neutrophil-chemoattractant agent is rash, such as follicular rash.

Rash can be quantified using the grades defined in the Common Terminology Criteria for Adverse Events (CTCAE), e.g. version 3.0, under the term "Rash/desquamation". As desquamation is not a common side effect of treatment with EGFR inhibition therapy, the patient's skin rash may be scored based on rash only. The CTCAE criterion for rash/desquamation can therefore suitably be adjusted as follows:

| CTCAE Grade | Description Term Rash |
|---|---|
| 1 | Macular or papular eruption or erythema without associated symptoms |
| 2 | Macular or papular eruption or erythema with pruritus or other associated symptoms |
| 3 | Widespread and confluent erythroderma or macular, papular, or vesicular eruption |
| 4 | Generalized exfoliative, ulcerative, or bullos dermatitis |
| 5 | Death |

A reduction in rash, e.g. of 10%, when used herein indicates is a statistically significant reduction of 10% in the total CTCAE score of a representative population, as compared to the same treatment with an anti-EGFR agent alone, i.e. without administration of an anti-neutrophil-chemoattractant agent. The reduction may be the result of prevention and/or treatment.

In a preferred embodiment of the method or use of the invention, the rash is reduced by at least 10%, such as at least 20%, e.g. at least 30%, such as at least 40%, e.g. at least 50%, such as at least 60%, e.g. at least 70%, such as at least 80%, e.g. at least 90%, such as least 95%.

Dosage Regimens

In the method and use of the invention, the anti-EGFR agent and the anti-neutrophil-attractant agent are given in an effective amount, i.e. in an amount effective, at dosages and for periods of time necessary, to achieve a desired result.

A therapeutically effective amount may vary according to factors such as the disease state, age, sex, and weight of the individual, and the ability of the agent to elicit a desired response in the individual.

An effective amount for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

The efficient dosages and the dosage regimens for the agents used in the present invention depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg.

In one embodiment, the agents used in the present invention may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In a preferred embodiment of the method of the invention, the anti-EGFR agent is an anti-EGFR antibody and the dosage regimen of the anti-EGFR antibody comprises administration, at least once per 14 days, of a dose of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg. More preferably, the administration of the anti-EGFR antibody is at least once per week.

In another embodiment of the invention, the anti-EGFR agent is an anti-EGFR antibody and the dosage regimen of the anti-EGFR antibody comprises administration, at least once per 14 days, of a dose of antibody of at least 5 mg, such as at least 10 mg, e.g. at least 25 mg, such as at least 50 mg, e.g. at least 75 mg, such as at least 100 mg, e.g. at least 150 mg, such as at least 200 mg, e.g. at least 250 mg, such as at least 300 mg e.g. at least 350 mg, such as at least 400 mg, e.g. at least 500 mg, such as at least 750 mg, e.g. at least 1000 mg, such as at least 1250 mg, e.g. at least 1500 mg, such as at least 2000 mg. More preferably, the administration of the anti-EGFR antibody is at least once per week.

In a further preferred embodiment, the total duration of the anti-EGFR treatment is at least one month, such as at least two months, e.g. at least four months, such as at least six months.

In another preferred embodiment of the method of the invention, the anti-neutrophil attractant agent is an anti-IL8 antibody and the dosage regimen of the anti-IL8 antibody comprises administration, at least once per 14 days, of a dose of antibody of at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg. More preferably, the administration of the anti-IL8 antibody is at least once per week.

In another embodiment of the invention, the anti-neutrophil attractant agent is an anti-IL8 antibody and the dosage regimen of the anti-IL8 antibody comprises administration, at least once per 14 days, of a dose of antibody of at least 5 mg, such as at least 10 mg, e.g. at least 25 mg, such as at least 50 mg, e.g. at least 75 mg, such as at least 100 mg, e.g. at least 150 mg, such as at least 200 mg, e.g. at least 250 mg, such as at least 300 mg e.g. at least 350 mg, such as at least 400 mg, e.g. at least 500 mg, such as at least 750 mg, e.g. at least 1000 mg, such as at least 1250 mg, e.g. at least 1500 mg, such as at least 2000 mg. More preferably, the administration of the anti-IL8 antibody is at least once per week.

In a further preferred embodiment, the total duration of the anti-IL8 treatment is at least one month, such as at least two months, e.g. at least four months, such as at least six months.

In some embodiments, the dosage regimen comprises administration, at least once per 14 days, of: a dose of anti-EGFR antibody, such as 2F8, of between 6 and 30 mg/kg and a dose of anti-IL8 antibody, such as 10F8, of between 5 and 20 mg/kg.

In other embodiments, the dosage regimen comprises administration, at least once per 14 days, of: a dose of anti-EGFR antibody, such as 2F8, of between 400 and 2500 mg/kg and a dose of anti-IL8 antibody, such as 10F8, of between 350 and 1500 mg/kg.

In some embodiments of the invention, the method of treatment is repeated after an interval of two months or more, such as three months or more, e.g. after six months or more.

The anti-EGFR agent and the anti-neutrophil-chemoattractant agent may be given simultaneously or sequentially in any order. In a preferred embodiment, both agents are administered on the same day. In another preferred embodiment, the anti-neutrophil-chemoattractant agent is administered at least one day before the anti-EGFR agent, such as at least two days, or at least three days before the anti-EGFR agent.

Compositions and Kits

In another aspect, the invention relates to a composition suitable for use in the above described methods, said composition comprising an anti-EGFR agent and an anti-neutrophil-chemoattractant agent, wherein said anti-neutrophil-chemoattractant agent is present in an amount sufficient to reduce one or more undesired dermatological side-effects of the anti-EGFR agent.

The two agents may in one embodiment be conjugated. For example, the agents may be combined in one molecule, such as a bivalent antibody capable of binding both EGFR and IL8. However, in another embodiment of said composition, said anti-EGFR agent and said anti-neutrophil chemoattractant agent are not conjugated.

In a further preferred embodiment, said composition is suitable for intravenous administration.

In another preferred embodiment, said composition comprises one or more further therapeutic agents selected from the group consisting of chemotherapeutic agents, immunosuppressive agents, anti-inflammatory agents, and anti-psoriasis agents.

In a further aspect, the invention relates to a kit of parts for use in the methods of invention described above, said kit of parts comprising: (i) a formulation comprising an anti-EGFR agent in admixture with a pharmaceutically acceptable adjuvant, diluent, or carrier; and (ii) a formulation comprising an anti-neutrophil-chemoattractant agent in an amount sufficient to reduce one or more undesired dermatological side-effects of the anti-EGFR agent in admixture with a pharmaceutically acceptable adjuvant, diluent, or carrier, wherein agents (i) and (ii) are each formulated for administration in conjunction with the other, and, optionally (iii instructions for the sequential, separate or simultaneous administration of the agents (i) and (ii) to a patient in need thereof.

Formulation, Additives and Mode-of-Administration

The pharmaceutical compositions and agents may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen composition of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding.

A pharmaceutical composition of the present invention may also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a composition in vivo and in vitro are well known in the art and may be selected by those of ordinary skill in the art.

The compositions of the present invention may be administered via any suitable route, such as an oral, nasal, inhalable, topical (including buccal, transdermal and sublingual), rectal, vaginal and/or parenteral route.

In some embodiments of the invention, the anti-EGFR agent and the anti-neutrophil-chemoattractant agent are given via the same route. In other embodiments, they are given by different routes.

In one embodiment of the method of the present invention, one of both agents is administered parenterally, preferably intravenously.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In a preferred embodiment, the pharmaceutical composition is administered by intravenous or subcutaneous injection or infusion.

In another embodiment, the compounds of the present invention are administered in crystalline form by subcutaneous injection, cf. Yang et al., PNAS USA 100(12), 6934-6939 (2003).

The pharmaceutical compositions of the present invention may be administered with medical devices known in the art. For example, in one embodiment, a pharmaceutical composition of the present invention may be administered with a needleless hypodermic injection device, such as the devices disclosed in U.S. Pat. No. 5,399,163 , 5,383,851, 5,312,335, 5,064,413, 4,941,880, 4,790,824, or U.S. Pat. No. 4,596, 556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions of the present invention may be formulated for particular routes of administration, such as oral, nasal, topical (including buccal, transdermal and sublingual), rectal, vaginal and/or parenteral administration. The pharmaceutical compositions may conveniently be presented in unit dosage form and may be prepared by any methods known in the art of pharmacy. The amount of active ingredient which may be combined with a carrier material to produce a single dosage form will vary depending upon the subject being treated, and the particular mode of administration. The amount of active ingredient which may be combined with a carrier material to produce a single dosage form will generally be that amount of the composition which produces a therapeutic effect. Generally, out of one hundred percent, this amount will range from about 0.01% to about 99% of active ingredient, such as from about 0.1% to about 70%, for instance from about 1% to about 30%.

Regardless of the route of administration selected, the compositions of the present invention, which may be used in the form of a pharmaceutically acceptable salt or in a suitable hydrated form are formulated into pharmaceutically acceptable dosage forms by conventional methods known to those of skill in the art. A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, di-ethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound used in the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols such as mannitol, sorbitol, glycerol or sodium chloride in the compositions Pharmaceutically acceptable diluents include saline and aqueous buffer solutions. The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. Compounds used in the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/micobacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic:polycytidylic acid.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption such as aluminum monostearate and gelatin.

Pharmaceutical compositions of the present invention may also include a suitable salt therefore. Any suitable salt, such as an alkaline earth metal salt in any suitable form (e.g., a buffer salt), may be used in the stabilization of the compound used in the present invention. Suitable salts typically include sodium chloride, sodium succinate, sodium sulfate, potassium chloride, magnesium chloride, magnesium sulfate, and calcium chloride. In one embodiment, an aluminum salt is used to stabilize a compound used in the present invention in a pharmaceutical composition of the present invention, which aluminum salt also may serve as an adjuvant when such a composition is administered to a patient.

Pharmaceutical compositions according to the present invention may be in a variety of suitable forms. Such forms include, for example, liquid, semi-solid and solid dosage forms, such as liquid solutions (e.g., injectable and infusible solutions), dispersions or suspensions, emulsions, microemulsions, gels, creams, granules, powders, tablets, pills, powders, liposomes, dendrimers and other nanoparticles (see for instance Baek et al., Methods Enzymol. 362, 240-9 (2003), Nigavekar et al., Pharm Res. 21(3), 476-83 (2004), microparticles, and suppositories.

The optima form depends on the chosen mode of administration, the nature of the composition, and the therapeutic application. Formulations may include, for instance, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing may be appropriate in treatments and therapies in accordance with the present invention, provided that the active ingredient in the pharmaceutical composition is not inactivated by the formulation and the formulation is physiologically compatible and tolerable with the route of administration. See also for instance Powell et al., "Compendium of excipients for parenteral formulations" PDA J Pharm Sci Technol. 52, 238-311 (1998) and the citations therein for additional information related to excipients and carriers well known to pharmaceutical chemists.

The compounds used in the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. For example, the blood-brain barrier (BBB) excludes many highly hydrophilic compounds. To ensure that the therapeutic compounds of the present invention cross the BBB (if desired), they may be formulated, for example, in liposomes. For methods of manufacturing liposomes, see for instance U.S. Pat. No. 4,522,811, 5,374,548 and U.S. Pat. No. 5,399,331. The liposomes may comprise one or more moieties which are selectively transported into specific cells or organs, thus enhance targeted drug delivery (see for instance V. V. Ranade J. Clin. Pharmacol. 29, 685 (1989)). Exemplary targeting moieties include folate or biotin (see for instance U.S. Pat. No. 5,416,016), mannosides (Umezawa et al., Biochem. Biophys. Res. Commun. 153, 1038 (1988)), antibodies (P. G. Bloeman et al., FEBS Lett. 357, 140 (1995), M. Owais et al., Antimicrob. Agents Chemother. 39, 180 (1995)), surfactant protein A receptor (Briscoe et al., Am. J. Physiol. 1233, 134 (1995)), different species of which may comprise the pharmaceutical compositions of the present inventions, as well as components of the invented molecules, p120 (Schreier et al., J. Biol. Chem. 269, 9090 (1994)), see also K. Keinanen, M. L. Laukkanen, FEBS Lett. 346, 123 (1994) and J. J. Killion, I. J. Fidler, Immunomethods 4, 273 (1994).

In one embodiment of the present invention, the compounds of the present invention are formulated in liposomes. In a further embodiment, the liposomes include a targeting moiety. In a further embodiment, the compounds in the liposomes are delivered by bolus injection to a site proximal to the desired area, e.g., the site of inflammation or infection, or the site of a tumor. The composition should be fluid to the extent that easy syringability exists. It should be stable under the conditions of manufacture and storage and should be preserved against the contaminating action of microorganisms such as bacteria and fungi.

In one embodiment, the compounds of the present invention may be formulated to prevent or reduce their transport across the placenta. This may be done by methods known in the art, e.g., by PEGylation of the compounds or by use of F(ab')$_2$ fragments. Further reference can be made to Cunningham-Rundles C et al., J Immunol Methods. 152, 177-190 (1992) and to Landor M., Ann Allergy Asthma Immunol 74, 279-283 (1995).

Combination Therapy

In further embodiments, the present invention provides methods which comprise administration of anti-EGFR agent and an anti-neutrophil-chemoattractant agent combined with one or more additional therapeutic agents as described below.

Thus, in one embodiment, the method of the invention comprises administration of one or more further therapies selected from chemotherapeutic agents, immunosuppressive agents, anti-inflammatory agents, anti-psoriasis agents, radiation therapy, hyperthermia, transplantation, surgery, sunlight therapy, and phototherapy.

In a further embodiment, the method comprises administration of one or more further therapies selected from the group consisting of nitrogen mustards, aziridines, alkyl sulfonates, nitrosoureas, platinum complexes, non-classical alkylating agents, folate analogs, purine analogs, adenosine analogs, pyrimidine analogs, substituted ureas, antitumor antibiotics, epipodophyllotoxins, microtubule agents, camptothecin analogs, enzymes, cytokines, monoclonal antibodies, recombinant toxins and immunotoxins, cancer gene therapies, cancer vaccines, radiation therapy, hyperthermia, transplantation, and surgery.

In an even further embodiment, the method comprises administration of one or more further therapies selected from the group consisting of immunosuppressive antibodies against MHC, CD2, CD3, CD4, CD7, CD28, B7, CD40, CD45, IFN-gamma, TNF-alpha, IL-4, IL-5, IL-6R, IL-7, IL-10, CD11a, CD20, and CD58 or antibodies against their ligands, soluble IL-15R, and IL-10.

In a yet further embodiment, the method comprises administration of one or more further therapies selected from the group consisting of cyclosporine, azathioprine, mycophenolic acid, mycophenolate mofetil, corticosteroids, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, transplantation, and surgery.

In an even further embodiment, the method comprises administration of one or more further therapies selected from the group consisting of aspirin, other salicylates, steroidal drugs, NSAIDs (nonsteroidal anti-inflammatory drugs), Cox-2 inhibitors, and DMARDs (disease modifying antirheumatic drugs).

In another embodiment, the method comprises administration of one or more further therapies selected from the group consisting of coal tar, A vitamin, anthralin, calcipotrien, tarazotene, corticosteroids, methotrexate, retinoids, cyclosporine, etanercept, alefacept, efaluzimab, 6-thioguanine, mycophenolate mofetil, tacrolimus (FK-506), hydroxyurea, sunlight therapy, and phototherapy.

In a preferred embodiment, the method comprises administration of one or more further therapies selected from: platinum derivatives, such as cisplatin or carboplatin; fluorouracil; paclitaxel, docetaxel and radiotherapy.

In a highly preferred embodiment, the method further comprises radiotherapy and/or administration of cisplatin or carboplatin.

The present invention is further illustrated by the following examples which should not be construed as further limiting.

EXAMPLES

Example 1

Study of the capacity of a locally injected IL8 antibody to prevent pustular rash induced by a locally injected EGFR antibody A study of the effect of local administration of an anti-IL8 antibody on follicular rash induced by administration of an anti-EGFr human antibody is performed in 2 stages. Each healthy volunteer participates in both stages.

Anti-EGFR antibody, e.g. 2F8, is provided in the following liquid formulation, buffered to pH 6.5:

| Ingredient | Concentration (mg/mL) |
| --- | --- |
| Anti EGFr antibody | 5 |
| Sodium Chloride, USP | 2.92 |
| Monobasic Sodium Phosphate, monohydrate, USP | 6.9 |
| Mannitol, USP | 30 |
| Polysorbate 80 | 0.2 |
| Water, USP | q.s. to 1 ml |

Anti-IL8 antibody, e.g. 10F8, is provided in the following liquid formulation, buffered to pH 6.5:

| Ingredient | Concentration |
| --- | --- |
| Anti IL-8 antibody | 5 mg/mL |
| Sodium Phosphate | 20 mM |
| Sodium Chloride | 50 mM |
| Mannitol | 3% |
| Tween-80 | 0.01% |
| Water | q.s. til 1 mL |

Stage 1

Stage 1 of the study is performed for dose-finding purposes. At the first treatment visit, 10 μg of anti-EGFR antibody is injected s.c. on the upper back of a healthy volunteer. The injection site is marked for later identification. At the next visit, 1 week later, the injection site is assessed for occurrence of rash. If no rash is present, another 10 μg is injected to the same site. At the same visit 100 μg is injected to another site marked for later identification. Each injection of anti-EGFR antibody is accompanied by a control injection of an identical volume of isotonic saline. This procedure takes place weekly, increasing the dose by a factor 10 for each week until a dose of 1 mg is reached, see Table 1. The patients are told to contact the investigator as soon as a rash occurs.

TABLE 1

Stage 1 - Dose Escalation Schedule - anti-EGFr Injections

| Stage 1 | Day 0 | Day 7 | Day 14 | Day 21 | Day 28 | Day 35 | Day 42 |
| --- | --- | --- | --- | --- | --- | --- | --- |
| Injection site 1 | — | 10 μg | 10 μg | 10 μg | 10 μg | — | — |
| Injection site 2 | — | — | 100 μg | 100 μg | 100 μg | 100 μg | — |
| Injection site 3 | — | — | — | 1 mg | 1 mg | 1 mg | 1 mg |

Stage 2

Stage 2 investigates the ability of anti-18 antibody to prevent anti-EGFr induced follicular rash. For each healthy volunteer the treatment schedule inducing rash during Stage 1 is repeated using a 10-fold increased dose of anti-EGFR antibody as compared to Stage 1. For each injection of anti-EGFR antibody, 0.25 mL anti-IL8 antibody at a concentration of 5 mg/mL is injected s.c. at the same injection site on the same day. During a period of 4 days following-each combined anti-EGFR/anti-IL8 administration, 0.25 ml anti-IL8 antibody is administered daily at the same injection site. FIG. 1 gives an overview the treatment of Stage 1 and Stage 2. There is a negative control for the rash inducing anti-EGFR antibody dose and there is a negative control for the anti-IL8 antibody dose as well.

Endpoints

Primary Endpoint

The degree of pustular rash at injection sites is judged by the investigator, and quantified using the grades defined in the Common Terminology Criteria for Adverse Events (CTCAE), e.g. version 3.0, under the term "Rash/desquamation". As desquamation is not a common side effect of treatment with EGFR inhibition therapy, the patient's skin rash is scored based on rash only. The CTCAE criterion for rash/desquamation is therefore adjusted as follows:

| CTCAE Grade | Description Term Rash |
|---|---|
| 1 | Macular or papular eruption or erythema without associated symptoms |
| 2 | Macular or papular eruption or erythema with pruritus or other associated symptoms |
| 3 | Widespread and confluent erythroderma or macular, papular, or vesicular eruption |
| 4 | Generalized exfoliative, ulcerative, or bullos dermatitis |
| 5 | Death |

Secondary Endpoints

The following analyses are made:
Photo documented pustular rash at injection sites
Histological assessment of
 Phenotype: Normal skin vs. follicular accumulation of neutrophil granulocytes
 Neutrophilic granulocytes: Elastase
 Cytokines: IL8, VEGF
 Angiogenesis: CD31, CD34, CD105, vWF

The invention claimed is:

1. A method for treating or rash associated with anti-EGFR treatment comprising:
   (a) identifying a subject who is undergoing anti-EGFR treatment and has a rash, wherein said anti-EGFR treatment comprises administering a quinazoline derivative or an antibody capable of binding to EGFR; and
   (b) administering, to the subject, an anti-IL8 antibody in an amount sufficient to treat or reduce the rash, wherein the antibody blocks the binding of IL8 to its receptor.

2. The method of claim 1, wherein said anti-EGFR treatment is for treating cancer.

3. The method of claim 2, wherein said cancer is selected from the group consisting of: breast cancer, bladder cancer, uterine/cervical cancer, esophageal cancer, pancreatic cancer, colorectal cancer, kidney cancer, ovarian cancer, prostate cancer, head and neck cancer, non-small cell lung cancer and stomach cancer.

4. The method of claim 2, wherein said cancer is head and neck cancer or non small-cell lung cancer.

5. The method of claim 1, wherein said anti-EGFR treatment comprises administering an antibody capable of binding to EGFR.

6. The method of claim 5, wherein said antibody binds to human EGFR with an equilibrium dissociation constant ($K_D$) of at most $10^{-8}$ M.

7. The method of claim 5, wherein the antibody is able to compete with an antibody comprising heavy and light chain variable region sequences set forth in SEQ ID NOs: 3 and 4, respectively.

8. The method of claim 5, wherein the anti-EGFR antibody is administered, at least once per 14 days, at a dose of at least 0.1 mg/kg.

9. The method of claim 8, wherein the anti-EGFR antibody is administered at least once per week.

10. The method of claim 8, wherein the anti-EGFR antibody is administered for a total duration of at least one month.

11. The method of claim 1, wherein said anti-EGFR treatment comprises administering a quinazoline derivative capable of binding to EGFR.

12. The method of claim 1, wherein the anti-IL8 antibody binds to human IL8 with an equilibrium dissociation constant ($K_D$) of at most $10^{-10}$ M.

13. The method of claim 1, wherein the anti-IL8 antibody is able to compete with an antibody comprising heavy and light chain variable region sequences set forth in SEQ ID NOs: 10 and 11, respectively.

14. The method of claim 1, wherein the anti-IL8 antibody is administered, at least once per 14 days, at a dose of at least 1.5 mg/kg.

15. The method of claim 14, wherein the anti-IL8 antibody is administered at least once per week.

16. The method of claim 14, wherein the anti-IL8 antibody is administered for a total duration of at least one month.

17. The method of claim 1, wherein said rash is reduced by at least 10%.

18. The method of claim 1, wherein an anti-EGFR treatment and the anti-IL8 antibody are administered on the same day.

19. The method of claim 1, wherein the anti-IL8 antibody is administered at least one day before an anti-EGFR treatment.

20. The method of claim 1, wherein the anti-EGFR treatment is administered parenterally.

21. The method of claim 1, wherein the anti-IL8 antibody is administered parenterally.

22. The method of claim 1, wherein said subject is a human being susceptible to developing rash when subjected to anti-EGFR treatment.

23. The method of claim 1, comprising administration of one or more further therapies selected from chemotherapeutic agents, immunosuppressive agents, anti-inflammatory agents, anti-psoriasis agents, radiation therapy, hyperthermia, transplantation, surgery, sunlight therapy, and phototherapy.

24. The method of claim 1, comprising administration of one or more further therapies selected from the group consisting of nitrogen mustards, aziridines, alkyl sulfonates, nitrosoureas, platinum complexes, non-classical alkylating agents, folate analogs, purine analogs, adenosine analogs, pyrimidine analogs, substituted ureas, antitumor antibiotics, epipodophyllotoxins, microtubule agents, camptothecin analogs, enzymes, cytokines, monoclonal antibodies, recombinant toxins and immunotoxins, cancer gene therapies, cancer vaccines, radiation therapy, hyperthermia, transplantation, and surgery.

25. The method of claim 1, comprising administration of one or more further therapies selected from the group consisting of immunosuppressive anti-bodies against MHC, CD2, CD3, CD4, CD7, CD28, B7, CD40, CD45, IFN-gamma, TNF-alpha, IL-4, IL-5, IL-6R, IL-7, IL-10, CD11a, CD20, and CD58 or antibodies against their ligands, soluble IL-15R, and IL-10.

26. The method of claim 1, comprising administration of one or more further therapies selected from the group consisting of cyclosporine, azathioprine, mycophenolic acid, mycophenolate mofetil, corticosteroids, methotrexate, gold salts, sulfasalazine, antimalarials, brequinar, leflunomide, mizoribine, 15-deoxyspergualine, 6-mercaptopurine, cyclophosphamide, rapamycin, tacrolimus, OKT3, anti-thymocyte globulin, transplantation, and surgery.

27. The method of claim 1, comprising administration of one or more further therapies selected from the group consisting of aspirin, salicylates, steroidal drugs, nonsteroidal anti-inflammatory drugs, Cox-2inhibitors, and disease modifying antirheumatic drugs.

28. The method of claim 1, comprising administration of one or more further therapies selected from the group consisting of coal tar, A vitamin, anthralin, calcipotrien, tarazotene, retinoids, etanercept, alefacept, efaluzimab, 6-thioguanine, hydroxyurea, sunlight therapy, and phototherapy.

29. The method of claim 5, wherein the anti-EGFR antibody is a human antibody.

30. The method of claim 5, wherein said anti-EGFR antibody comprises heavy and light chain variable regions having the amino acid sequence set forth in SEQ ID NOs: 3 and 4, respectively.

31. The method of claim 5, wherein the anti-EGFR antibody comprises a) heavy chain CDR1, CDR2, and CDR3 sequences comprising the amino acid sequences set forth in SEQ ID NOs:5, 6, and 1, respectively; and (b) light chain CDR1, CDR2, and CDR3 sequences comprising the amino acid sequences set forth in SEQ ID NOs:7, 8, and 9, respectively.

32. The method of claim 1, wherein said antibody comprises heavy and light chain variable regions having the amino acid sequence set forth in SEQ ID NOs: 10 and 11, respectively.

33. The method of claim 1, wherein said anti-IL8 antibody comprises a) a heavy chain variable region comprising CDR1, CDR2, and CDR3sequences comprising the amino acid sequences set forth in SEQ ID NOs:12, 13, and 2, respectively; and (b) a light chain variable region comprising CDR1, CDR2, and CDR3 sequences comprising the amino acid sequences set forth in SEQ ID NOs:14, 15, and 16, respectively.

34. The method of claim 12, wherein said antibody binds to human IL8 with an equilibrium dissociation constant ($K_D$) of at most $10^{-10}$ M.

* * * * *